United States Patent
Cole et al.

(10) Patent No.: US 6,743,212 B1
(45) Date of Patent: *Jun. 1, 2004

(54) MULTI-LAYERED TAMPON COVER

(75) Inventors: Robert Cole, Jackson, NJ (US); Lai-Hing Louie, Kendall Park, NJ (US); Linda M. Pierson, Hillsborough, NJ (US); Mary S. Yeganeh, Piscataway, NJ (US)

(73) Assignee: McNeil, PPC, Inc., Skillman, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 109 days.

(21) Appl. No.: 08/997,676

(22) Filed: Dec. 23, 1997

(51) Int. Cl.[7] .................................................. A61F 13/20
(52) U.S. Cl. .............. 604/385.17; 604/904; 604/385.18
(58) Field of Search ................... 604/378, 904, 604/363, 385.17, 385.18

(56) References Cited

U.S. PATENT DOCUMENTS

| | | | |
|---|---|---|---|
| 2,328,795 A | * 9/1943 | Finkes | 604/904 |
| 2,330,257 A | * 9/1943 | Bailey | 604/904 |
| 3,340,874 A | * 9/1967 | Burgeni | 604/15 |
| 4,056,103 A | 11/1977 | Kaczmarzyk et al. | |
| 4,274,412 A | * 6/1981 | Austin | 604/904 |
| 4,305,391 A | 12/1981 | Jackson | |
| 4,475,911 A | 10/1984 | Gellert | |
| 4,578,070 A | 3/1986 | Holtman | |
| 4,755,179 A | 7/1988 | Shiba et al. | |
| 4,798,603 A | 1/1989 | Meyer et al. | |
| 4,883,707 A | 11/1989 | Newkirk | |
| 5,135,521 A | 8/1992 | Luceri et al. | |
| 5,374,258 A | 12/1994 | Lloyd et al. | |
| 5,403,300 A | 4/1995 | Howarth | 604/384 |
| 5,567,376 A | 10/1996 | Turi et al. | 264/455 |
| 5,591,149 A | 1/1997 | Cree et al. | 604/378 |
| 5,643,240 A | 7/1997 | Jackson et al. | 604/378 |
| 5,728,081 A | * 3/1998 | Baer et al. | 604/370 |
| 5,752,945 A | 5/1998 | Mosley et al. | 604/370 |
| 5,817,077 A | * 10/1998 | Foley et al. | 604/363 |
| 5,928,184 A | * 7/1999 | Etheredge et al. | 604/15 |
| 6,315,763 B1 | * 11/2001 | Albright et al. | 604/385.18 |

FOREIGN PATENT DOCUMENTS

| | | |
|---|---|---|
| EP | 0 685 215 A1 | 12/1995 |
| GB | 2 292 526 A | 2/1996 |
| WO | WO 98/46182 | 10/1998 |

* cited by examiner

Primary Examiner—Weilun Lo
Assistant Examiner—Jacqueline F Stephens

(57) ABSTRACT

The present invention relates to a tampon having an absorbent structure and a multilayered cover substantially enclosing the absorbent structure. The cover has an outer layer capable of retaining liquid and an inner layer disposed between the outer layer and the absorbent structure. The inner layer creates a controlled interruption of fluid flow between the outer layer and the absorbent structure. This interruption allows the outer layer retains sufficient liquid to minimize vaginal wall drying prior to saturation of the absorbent structure.

13 Claims, 3 Drawing Sheets

MULTI-LAYERED TAMPON COVER

FIELD OF THE INVENTION

The present invention generally relates to a catamenial tampon having a multi-layered cover and an absorbent core. The outer surface of the cover is wettable to provide a moist surface against the vaginal wall, while inner regions of the cover disrupt immediate liquid flow into the absorbent core. This structure decreases the likelihood that the tampon will desiccate the surface of the vaginal wall.

BACKGROUND OF THE INVENTION

Catamenial tampons are generally used to absorb menstrual fluid of women during the menstrual cycle. Usually, menstrual flow varies during the cycle, and there are often days of relatively light flow at the beginning and end of the cycle. On light flow days, there is little excess fluid available for a tampon to absorb in the vaginal cavity, and conventional tampons may absorb too much fluid, desiccating the vaginal wall or mucosa. This can cause discomfort during the insertion and removal of these tampons.

The area of the vaginal cavity of major concern relating to the desiccation is the upper layer of cells in the vaginal mucosa, the squamous epithelium. Under non-menstrual conditions, the vaginal wall is lubricated by secretions that pass through the vagina: fluids and mucus flowing from the cervix and hormone-controlled secretions originating in the uterus. The natural exfoliation of vaginal epithelial cells also contributes to the natural moisture in the vaginal cavity and the squamous epithelium.

When a conventional tampon absorbs the natural moisture from between the cells in the squamous epithelium on light flow days of the menstrual cycle, the cells are rendered more susceptible to being peeled off prematurely. This peeling is called desquamation, and it can occur in removal of the tampon prior to its saturation. First, the initial release of an unsaturated conventional tampon can be quite painful, as some of the squamous cells may have become "attached" to the conventional tampon as it absorbs the natural moisture. Next, the dry, absorbent surface of the conventional tampon can drag along other portions of the relatively dry squamous epithelium causing additional pain.

These conventional tampons often have a cover disposed on the majority of the surface of the absorbent structure to contain absorbent materials therein. An example of such a cover can be seen in Friese, U.S. Pat. No. 4,816,100, which uses a nonwoven cover. Several attempts have been made to improve tampon covers. One attempt is illustrated in Jackson, U.S. Pat. No. 4,305,391, which employs a combination of two wrapping layers to form a cover. The outer wrap has a substantially greater pore size than the inner wrap. Purportedly, this allows fluid to rapidly pass through the outer wrap before it is partially absorbed and more slowly passed through the inner wrap of the cover. This arrangement of a porosity gradient or suction gradient is conventionally used to better isolate fluids within the tampon to reduce reverse flow from the absorbent core to the surface of the cover.

Another attempt to reduce the pain associated with the removal of tampons is disclosed in Jackson, U.S. Pat. No. 4,335,722. This attempt employs a water dispersible barrier layer around a strongly absorbent core containing superabsorbent material. This absorbent structure is then covered with a non-superabsorbent material, such as rayon. In this construction, the absorbent core is utilized only after the outer layer is saturated. Then, fluid from the saturated cover is available to disperse the barrier layer. However, once the barrier layer is dispersed, a conventional suction pressure gradient draws fluid into the core from the cover.

Finally, Kaczmarzyk et al., U.S. Pat. No. 4,056,103, discloses a fluid-permeable cover with sufficient absorbent capacity and capillary suction to successfully compete with the suction pressure of a superabsorbent-containing core to maintain a soft, lubricious condition during use. Unfortunately, these three attempts provide a conventional capillary suction pressure gradient which strongly draws liquids into the tampon using covers which may themselves sufficiently dry the squamous epithelium to cause pain and trauma during use.

A different approach is disclosed in Foley et al., EP 685215, which reduces the capillary suction pressure that a tampon exerts on the vaginal walls to remove excess menstrual fluid while limiting the vaginal drying which can occur. This may be accomplished by using multiple cover layers, possibly hydrophobic, to separate the absorbent core from the vaginal wall during use. While this advance is significant, the outer surface of the tampon is likely to be relatively dry.

Therefore, what is needed is a tampon having reduced suction pressure to avoid drawing too much of the natural moisture from the squamous epithelium and which maintains a moist outer surface throughout use to provide a non-drying tampon for catamenial use.

SUMMARY OF THE INVENTION

Understanding the discomfort and pain associated with tampon insertion and removal has led to the invention of a tampon which keeps the vaginal wall naturally moist. The unique structure of this improved cover substantially reduces vaginal drying by maintaining the natural moisture of the vaginal wall. Additionally, insertion and removal comfort can be further enhanced by a smooth surface presented by the outer layer of a multilayered cover.

Thus, the present invention relates to a tampon having an absorbent structure and a multilayered cover substantially enclosing the absorbent structure. The cover has an outer layer capable of retaining liquid and an inner layer disposed between the outer layer and the absorbent structure. The inner layer creates a controlled interruption of fluid flow between the outer layer and the absorbent structure. This interruption allows the outer layer to retain sufficient liquid to minimize vaginal wall desiccation/drying prior to saturation of the absorbent structure.

DETAILED DESCRIPTION OF THE PREFERRED EMBODIMENT

Figure 1:
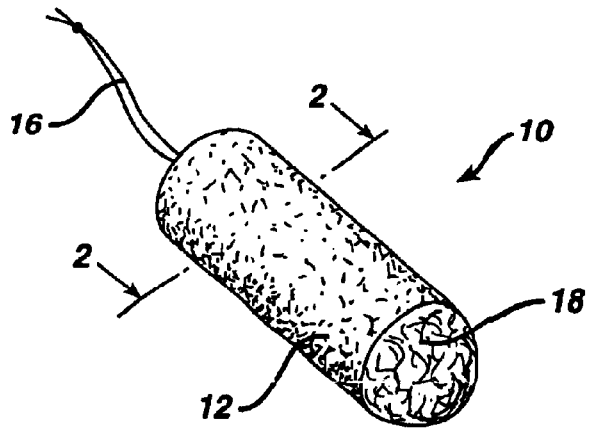
FIG. 1 is a perspective view of a tampon according to the present invention.
Figure 2:
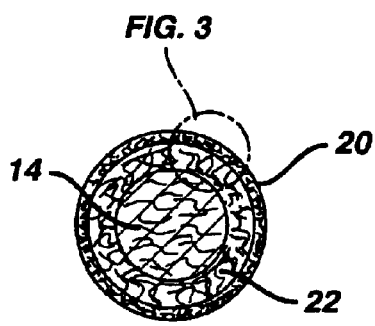
FIG. 2 is a cross-section along line 2—2 of FIG. 1.

Referring to FIGS. 1 and 2, the tampon 10 includes a multilayered cover 12 substantially enclosing an absorbent structure or core 14, and a withdrawal string 16. In the embodiment of FIG. 1, the multilayered cover 12 does not cover a rounded insertion end 18. However, this may be enclosed in other embodiments. The multilayered cover 12 has at least two layers, an outer layer 20 and at least one inner layer 22. The outer layer 20 preferably provides a smooth surface to aid in insertion and withdrawal of the tampon 10 during use. The inner layer(s) 22 is/are constructed in a manner to create a controlled interruption of fluid flow. The controlled interruption may be achieved by creating a porosity gradient between the outer layer 20 and the inner layer(s) 22 from relatively small pores in the outer layer 20 to relatively larger pores in the inner layer(s) 22. It may also be achieved by a relatively more hydrophilic outer layer 20 and relatively less hydrophilic inner layer(s) 22.

Figure 3:
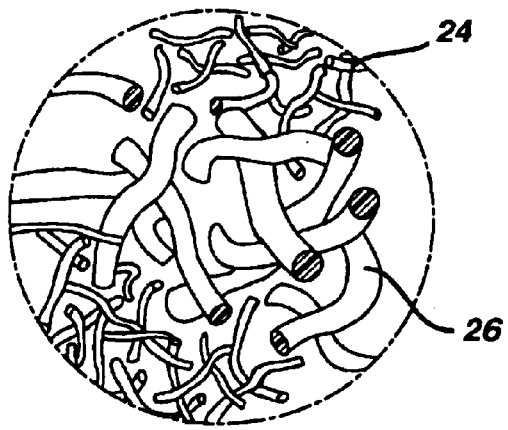
FIG. 3 is an enlarged view of a portion of the cross-section of FIG. 2.
Figure 4:
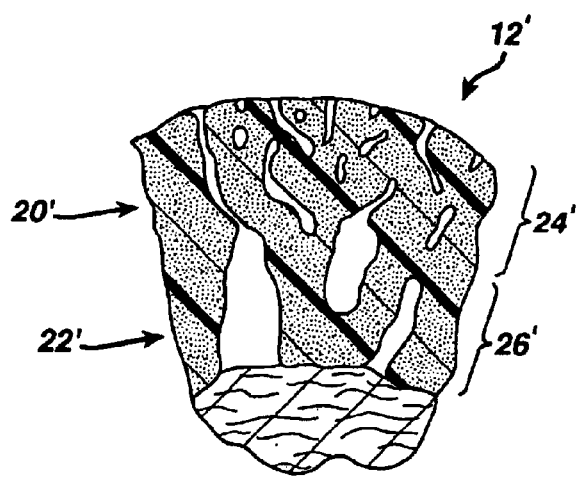
FIG. 4 is an enlarged view of an alternative embodiment of the present invention employing a foamed cover.

In a preferred embodiment, the outer layer 20 can be formed of relatively low denier fibers 24 which form relatively small inter-fiber pores as shown in FIG. 3. These low denier fibers 24 are hydrophilic. There are several recognized tests to determine hydrophilicity. One such test is the contact angle with water. Preferably, the fibers have a contact angle in water of less than about 90°. They may be synthetic, such as synthetic cellulosic fibers and polymeric fibers, or they may be natural, such as cotton, wood pulp, wool, silk, and the like. Useful synthetic cellulosic fibers include rayon and lyocell. Useful polymeric fibers include bicomponent fibers, polyolefin fibers, polyester fibers, polyamide (including nylon), polyacrylic, and the like. If the fibers are not hydrophilic per se, they can be rendered hydrophilic by appropriate treatments and/or finishes.

The inner layer(s) 22 can be formed of higher denier fibers 26 which form relatively larger inter-fiber pores as shown in FIG. 3. These higher denier fibers 26 are hydrophilic, and they may be less hydrophilic than the low denier fibers 24 of the outer layer 20. The same general categories of fibers may be used for the inner layer(s) 22 as those described above for the outer layer 20. Again, if the fibers are not hydrophilic per se, they can be rendered hydrophilic by appropriate treatments and/or finishes.

If more than one inner layer 22 is employed, the additional layers should be compatible with the ability of the first inner layer 22 to interrupt "fluid connectivity" between the outer layer 20 and the absorbent structure 14 as described below. Preferably, the additional inner layers have a similar pore size or even a greater pore size than a first inner layer.

Figure 7:
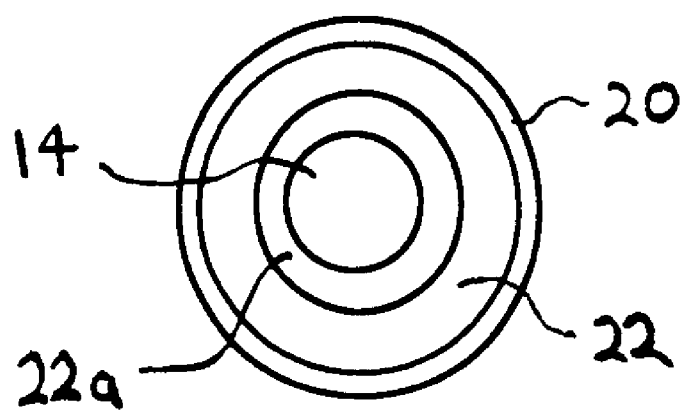
FIG. 7 is a cross-section taken along line 2—2 of FIG. 1, illustrating an alternative embodiment of the present invention employing an additional inner layer compared to that which is shown in FIG. 2.

An additional inner layer 22a is shown in FIG. 7. disposed between inner layer 22 and absorbent structure 14.

The inner layer(s) 22 may also be formed of apertured films. These apertured films may be two-dimensional films such as are generally described in Mattingly, III, et al., U.S. Pat. No. 4,690,679, but preferably, they are three-dimensional films such as are generally described in Thompson, U.S. Pat. No. 3,929,135.

The multilayered cover 12 of the present invention can be formed by carding first web of relatively high denier fiber, such as polyethylene/polyester bicomponent fibers, or a mixture of such fibers with other resilient fibers such as polyester, on a moving belt or screen. This first web will form the inner layer 22. A second web of lower denier fibers can then be carded onto the moving first web. This second web will form the outer layer 22. The resulting multilayered nonwoven web can then be thermally bonded by drawing hot air through the web and moving belt. This through-air bonding can occur with a second restraining belt laid to substantially enclose the multilayered nonwoven web, a double-belt system, or in the absence of such a restraining belt, a single-belt system. A conventional belt, e.g., 40×40 mesh, can be used to carry the carded webs. However, finer mesh belts, such as 80×80 or 100×100, can produce a smoother fabric surface, and coarser mesh belts, such as 20×20, can produce a loftier fabric layer.

Different multilayered covers can be formed by combining the inner and outer layers by lamination, thermobonding point bonding, needle-punching, hydroentangled, adhesives, and the like. This may be necessary to combine different, layers such as nonwoven with apertured film, nonwoven with foam, and the like.

In an alternative embodiment, the multilayered cover 12 is formed of a multilayered or multi-zoned foam structure 12'. In this embodiment, the outer layer 20' has relatively narrow pores 24', while the inner layer 22' has relatively large pores 26'. Foams of this type can be created by optimizing and selectively controlling the foam components and the foaming process conditions such as viscosity, temperature, amount of blowing agent and surfactants. The pore size gradient in foams may be more gradual than achieved by combining separate, discrete layers. However, multiple layers of foamed material may be combined, e.g. through lamination.

Alternatively, it is possible to employ an open cell foam as only the inner layer(s) 22. Preferably, the foam has about 30 to about 60 pores per linear inch (ppi). The foam material is not critical to the invention, and a exemplary, non-limiting list of useful foams may include polyurethane, poly(vinyl alcohol), cellulose sponge, and the like. Polyurethane may be treated to provide the desired hydrophilicity, while poly (vinyl alcohol) is inherently hydrophilic. Such foams are commercially available through suppliers such as Foamex of Eddystone, Pa., USA.

There are a number of available techniques useful to measure the average pore size of a nonwoven material. These techniques include the use of the liquid extrusion cell, developed at Textile Research Institute, Princeton, N.J., USA. This technique has been described in Miller et al., "An Extended Range Liquid Extrusion Method for Determining Pore Size Distributions", Textile Research Journal, Vol. 56, pp. 35–40 (1986), herein incorporated by reference, and it was used to derive a mathematical model to predict the average pore size of a nonwoven fabric, Cohen, "A Wet Pore-Size Model for Coverstock Fabrics", *Book of Papers: The International Nonwoven Fabrics Conference, INDA-TEC'90*, Association of the Nonwoven Fabrics Industry, pp. 317–330 (1990), herein incorporated by reference. Based on this model, the following equation was used in the determination of average pore sizes reported in the specification:

$$r = (S_f x_i a^2 / S_f x_i a)((r_f / x r_w) - 1)/t \qquad (I)$$

wherein r is the average pore radius;

a is the fiber radius;

x is a number fraction;

$x_i$ is the ratio of dry fabric density to wet fabric density;

$r_f$ is the fiber density;

$r_w$ is the dry fabric density; and t is the tortuosity parameter. Based upon Cohen's work, the ratio 1.2 was selected for x, and 1.44 was selected as t.

Additional means for determining the pore sizes of the cover layers include measuring open area via the image analysis method described below in Example 1 and determination of "ECD" as described in Chen et al., U.S. Pat. No. 5,037,409, herein incorporated by reference. The most suitable measurement will be influenced by the type and the thickness of the layers.

The multilayered cover 12 preferably has a basis weight of about 20 g/m² (gsm) to about 80 gsm, more preferably, about 30 gsm to about 60 gsm, and most preferably, about 35 gsm (1 ounce/yd²) to about 50 gsm. The outer layer 20 should be sufficiently thick to provide sufficient absorbent capacity to provide a moist surface, but not thick enough to hinder the transfer of fluids into the absorbent structure 14.

The inner layer(s) 22 should be sufficiently thick to provide sufficient separation between the outer layer 20 and the absorbent structure 14 to disrupt fluid connectivity, but not thick enough to prevent fluid connectivity when the outer layer 20 approaches or exceeds fluid saturation. Preferably, the ratio of the thickness of a fibrous outer layer to the thickness of a fibrous inner layer is between about 1:1 to about 1:4, more preferably, between about 1:2 to about 1:3.

Figure 5:
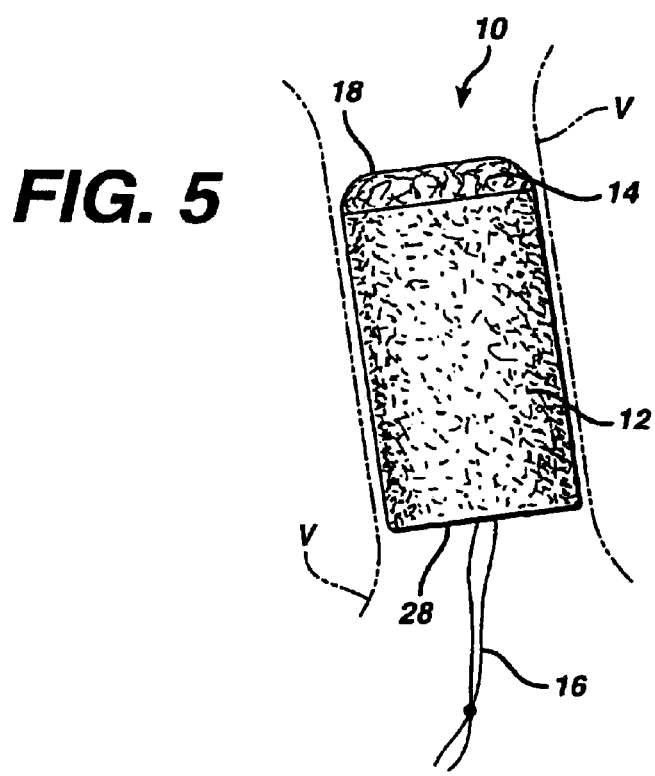
FIG. 5 is a side view of a tampon according to the present invention during use.

As mentioned above, the cover 12 substantially encloses the absorbent structure 14. It is preferred that the cover 12 is present on most of the surface of the absorbent structure 14 which can contact the vaginal wall (V) during use. This is illustrated in FIG. 5 which shows a tampon 10 according to the present invention in use in an expanded state after having absorbed some menstrual fluid. It is not necessary that the cover 12 enclose the domed insertion end 18 or the withdrawal end 28, as these surfaces provide minimal of the surface area for contact between the tampon 10 and the vaginal wall (V).

The cover 12 may be physically attached to the absorbent structure 14 or it may simply form a pouch which completely encloses the absorbent structure 14. Examples of the former may be by thermobonding to the outer surface of the absorbent structure 14, as disclosed in Friese, U.S. Pat. No. 4,816,100, which is herein incorporated by reference; by embedding one end of the cover 12 into the interior of the absorbent structure 14, as disclosed in William's, WO 95/16423, which is herein incorporated by reference; by folding at least a portion of the cover 12 around a sliver which is wound to form the absorbent structure 14, as disclosed in Brown, U.S. Pat. No. 5,185,010, which is herein incorporated by reference; by wrapping the cover 12 around the absorbent structure 14, as disclosed in Heinemann et al., U.S. Pat. No. 5,004,467, which is herein incorporated by reference; by needle-punching the cover 12 and absorbent structure 14 together; and by any other method or structure which combines the cover 12 and absorbent structure 14 to form a tampon 10.

The structure of the absorbent core 14 is not critical to the practice of the present invention. Preferably, the absorbent core 14 is a spirally wound core as described in EP 422,660, corresponding to U.S. Ser. No. 07/596,454, filed Oct. 12, 1990 now abandoned, the disclosure of which is hereby incorporated by reference. Other absorbent structures 14 which may be useful in the practice of the present invention include those tampon structures commercially available under the "TAMPAX", "PLAYTEX", and "KATE"brands. While these tampon structures are fibrous, including natural and/or synthetic fibers, it is also possible to use other materials in the absorbent structure 14, including foams, sellable materials, such as superabsorbents, and the like. Preferably, the absorbent structure 14 contains absorbent cellulosic fibers 30 such as cotton and/or rayon. These fibers are both absorbent and generally of low denier or fiber cross-section to create small pores and/or capillaries between the fibers to absorb and contain menstrual fluid. Thus, the absorbent structure 14 strongly contains the absorbed fluids.

Figure 6:
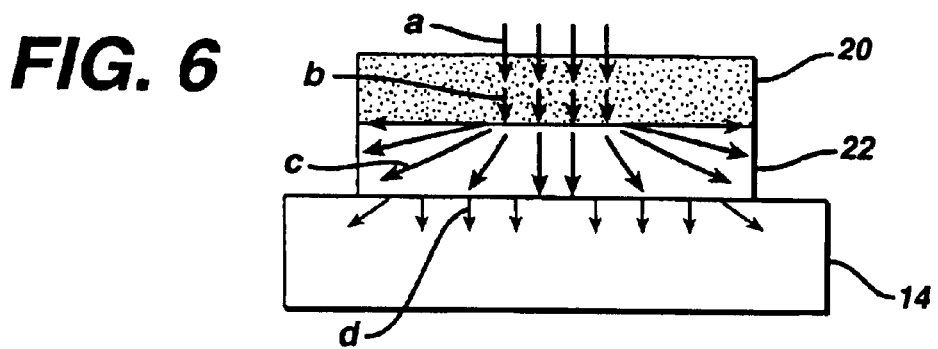
FIG. 6 is a diagram of fluid flow in a tampon according to the present invention.

It is believed that the relatively small pores in the outer layer 20 provide a small reservoir and the relatively large pores in the inner layer(s) 22 provide a mechanism to interrupt "fluid connectivity" between the outer layer 20 and the main fluid reservoir, the absorbent structure 14. This phenomenon is illustrated in the FIG. 6. This fluid disconnection allows the surface of the tampon 10 to quickly become substantially saturated with a very small amount of fluid. Because the outer layer 20 does not have a large absorbent capacity, it is not likely to dry out the vaginal wall when used during light flow days of the menstrual cycle. However, it is believed that as an area of the outer layer 20 becomes saturated and substantially all of the pores in this area become filled with fluid, a critical breakthrough point is reached, illustrated by the arrows at (a) and (b) in FIG. 6. Just after critical breakthrough, the fluid "overflows" into the inner layer(s). The fluid can travel faster in the larger pores of the inner layer(s) 22, and it can be transported directly to the absorbent structure 14 to provide fluid connectivity between the outer layer 20 of the cover 12 and the absorbent structure 14, as shown by the downward arrows at (c).

In addition, if the immediate volume of the absorbent structure 14 has already absorbed fluid, the newly received fluid may travel along the inner layer(s) 22 of the cover 12, as shown by the more horizontal arrows at (c), to a relatively unused volume of the absorbent structure 14. When the fluid reaches the absorbent fibers 30 of the core with their small interfere pores or fine capillaries, the fluid becomes substantially "locked" into the absorbent structure 14 at (d) in FIG. 6. As the absorbent structure 14 removes fluid from the inner layer(s) 22, the fluid connectivity can be disrupted, and the capillary suction provided by the absorbent structure 14 is prevented from acting directly upon the vaginal wall (V). This process of establishing and then interrupting the fluid connectivity between the outer layer 20 and the absorbent structure 14 can be repeated many times during the use of the tampon 10. Thus, it is believed that the interaction of the outer layer 20, inner layer(s) 22 and absorbent structure 14 keeps the vaginal wall (V) naturally moist by functioning like a pump with a check valve. When the "pump" is primed with a continuous column or stream of liquid between the outer layer 20 and absorbent structure 14, liquid will flow into the absorbent structure 14. However, when this process substantially drains the inner layer(s) 22, there is a fluid disconnection. No matter how much additional capacity the absorbent structure 14 may have, because there is not fluid connectivity with the outer layer 20, the structure 14 cannot pull in fluid.

The tampons of the present invention can be used with an applicator or an inserter, or they may be digitally inserted, without an applicator.

EXAMPLES

The present invention will be further understood by reference to the following specific Examples which are illustrative of the composition, form and method of producing the multilayered cover of the present invention. It is to be understood that many variations of composition, form and method of producing the cover would be apparent to those skilled in the art. The following Examples, wherein parts and percentages are by weight unless otherwise indicated, are only illustrative.

Example 1

A commercially available tampon, o.b.™ Super Absorbency having a 8.5 gsm 3 denier bicomponent cover, a similarly constructed tampon according to the present invention having a 40 gsm multilayered cover ("Tampon A"), and a similarly constructed tampon having a 40 gsm 3 denier bicomponent cover were tested to compare performance differences ("Tampon B"). The 40 gsm multilayered cover had an outer layer (approximately 55 wt-% of the cover) of 100 wt-% 3 denier bicomponent (polyethylene over polyethylene terephthalate (PE/PET)) and an inner layer (approximately 45 wt-% of the cover) of 66 wt-% 15 denier PET and 34 wt-% 10 denier PE/PET bicomponent fibers and was formed in a double belt through-air bonding process.

The % Open Area can be used to estimate the relative porosity of the two layers of Tampon A. The percent open area of each layer was determined with a top light, photomicrography equipment, and ImagePro™ Plus computer analysis program. Each side was analyzed by focusing on the layer of interest and adjusting the conditions to minimize interference from the other layer. The results for the open area of the inner layer and outer layers were 17.9% (std. de. 3.2%) and 59.3% (std. de. 5.0%), respectively.

First, cross-sections of tampons were mounted in a rubber mount leaving about 1 mm of the tampon exposed and examined at 75× magnification while synthetic menstrual fluid was added using a Drummond Wiretral ten microliter capillary delivery system. 2–3 drops of fluid were added to each sample. (each drop was about 2 microliters) and allowed to reach equilibrium within the sample. After 5 minutes, fluid was seen in the cover outer layer of Tampon A, and the inner cover layer was relatively clean. In contrast, the commercial tampon and Tampon B had some fluid wicking into the absorbent core.

In a simulation of light flow absorption, blotter paper was wrapped around new tampon cross-sections (20 mm length) and secured with a #8 rubber band, approximately 2 mm from the top of the tampon sections. The upper edge of the blotter paper extended just above the tampon section to prevent fluid overflow. Synthetic menstrual fluid was added to the blotter paper using a 20 microliter capillary tube. First, 20 microliters was added and allowed to be absorbed. A second 20 microliter addition of fluid was added to saturate the blotter paper. The blotter paper was pressed to determine whether fluid would breakthrough from the cover to the core. Finally, an additional 20 microliters was added to oversaturate the blotter paper. Observations of the procedure were recorded.

Neither Tampon A, Tampon B, nor the commercial tampon absorbed fluid from the blotter paper into the core without the external pressure. With the external pressure, the commercial tampon cover and Tampon B wicked fluid into the absorbent core. In contrast, the outer layer of Tampon A became filled with fluid, but the inner layer prevented the fluid from immediately wicking into the absorbent core. Only after the inner layer became filled with fluid did fluid wick into the core. More pressure was required to induce fluid to be absorbed into the core. During higher fluid add-on levels, all three tampons exhibited similar rapid wicking of fluid through the cover into the core.

Example 2

A 45° angle run-off test was performed with a piece of blotter paper over which a cover material was placed. Saline fluid was introduced at a constant rate from a burette onto the test sample until fluid ran off. The following samples were tested: 8.5 gsm 3 denier bicomponent cover (Control), 40 gsm single-belt cover with 100 wt-% 3 denier PE/PET bicomponent fibers in outer layer and with 50 wt-% 15 denier PET and 50 wt-% 10 denier PE/PET bicomponent fibers in the inner layer, 40 gsm double-belt cover with 100 wt-% 3 denier PE/PET bicomponent in outer layer and with 66 wt-% 15 denier PET and 34 wt-% 10 denier PE/PET bicomponent fibers in the inner layer. The latter two materials are examples of the present invention. The results are shown below:

| Cover Material | Cover Weight (g) | Run-Off Time (sec) | Cover Retention Capacity (g/g) |
|---|---|---|---|
| 8.5 gsm 3 d. Bico | 0.10 | 50.0 | 1.1 |
| 40 gsm Single-Belt 100%/(50%/50%) | 0.40 | 195.7 | 6.5 |
| 40 gsm Double-Belt 100%/(66%/34%) | 0.44 | 421.7 | 8.5 |

A review of the results shows a significant increase in run-off time and enhanced fluid retention capacity by the covers according to the present invention.

The specification and examples above are presented to aid in the complete and non-limiting understanding of the invention disclosed herein. Since many variations and embodiments of the invention can be made without departing from its spirit and scope, the invention resides in the claims hereinafter appended.

What is claimed is:

1. A tampon designed and configured for placement against a vaginal wall, comprising an absorbent structure and a multilayered cover substantially enclosing the absorbent structure, the cover comprising an outer layer capable of retaining liquid and an inner layer disposed between the outer layer and the absorbent structure; wherein the inner layer provides a structure that is capable of repeatedly providing and interrupting fluid flow between the outer layer and the absorbent structure whereby the outer layer retains sufficient liquid to minimize vaginal wall drying prior to saturation of the absorbent structure; and wherein the outer layer has a first average pore size, the inner layer has a second average pore size, and the second average pore size is greater than the first average pore size.

2. The tampon of claim 1 wherein the absorbent structure has a third average pore size that is less than the second average pore size.

3. The tampon of claim 1 wherein the multilayered cover comprises foam material.

4. A tampon comprising an insertion end; a withdrawal end; a withdrawal string extending from the withdrawal end; an absorbent structure and a multilayered cover substantially enclosing the absorbent structure, the cover comprising (a) a fibrous outer layer having a first average pore size and being capable of retaining liquid and (b) a fibrous inner layer having a second average pore size and disposed between the outer layer and the absorbent structure; wherein the second average pore size is greater than the first average pore size and the inner layer creates a controlled interruption of fluid flow between the outer layer and the absorbent structure whereby the outer layer retains sufficient liquid to minimize vaginal wall drying prior to saturation of the absorbent structure.

5. The tampon of claim 4 wherein the absorbent structure has a third average pore size that is less than the second average pore size.

6. The tampon of claim 4 wherein the outer layer has a thickness, the inner layer has a thickness, and a ratio of the thickness of the outer layer to the thickness of the inner layer is between about 1:1 to about 1:4.

7. The tampon of claim 4 which further comprises an additional layer disposed between the inner layer and the absorbent structure.

8. The tampon of claim 4 wherein the outer layer comprises a fibrous nonwoven web comprising polyolefin fibers having a first average denier, the inner layer comprises a fibrous nonwoven web comprising polyolefin fibers having a second average denier, wherein the second average denier is greater than the first average denier.

9. A tampon designed and configured for placement against a vaginal wall, comprising an absorbent structure and a multilayered cover substantially enclosing the absorbent structure, the cover comprising an outer layer capable of retaining liquid and an inner layer disposed between the outer layer and the absorbent structure, and which further comprises an additional layer disposed between the inner layer and the absorbent structure; wherein the inner layer provides a structure that is capable of repeatedly providing and interrupting fluid flow between the outer layer and the absorbent structure whereby the outer layer retains sufficient liquid to minimize vaginal wall drying prior to saturation of the absorbent structure.

10. A tampon designed and configured for placement against a vaginal wall, comprising an absorbent structure and a multilayered cover substantially enclosing the absorbent structure, the cover comprising an outer layer capable of retaining liquid and an inner layer disposed between the outer layer and the absorbent structure and which further comprises an additional layer disposed between the inner layer and the absorbent structure; wherein the inner layer creates a spacer that is capable of repeatedly providing and interrupting fluid flow between the outer layer and the absorbent structure in conditions of low fluid availability whereby the outer layer retains sufficient liquid to minimize vaginal wall drying prior to saturation of the absorbent structure.

11. A tampon designed and configured for placement against a vaginal wall, comprising an absorbent structure and a multilayered cover substantially enclosing the absorbent structure, the cover comprising an outer layer capable of retaining liquid and an inner layer disposed between the outer layer and the absorbent structure; wherein the inner layer provides a structure that is capable of repeatedly providing and interrupting fluid flow between the outer layer and the absorbent structure whereby the outer layer retains sufficient liquid to minimize vaginal wall drying prior to saturation of the absorbent structure; and wherein the outer layer comprises a fibrous nonwoven web comprising polyolefin fibers having a first average denier, the inner layer comprises a fibrous nonwoven web comprising polyolefin fibers having a second average denier, wherein the second average denier is greater than the first average denier.

12. The tampon of claim 11 wherein the outer layer has a thickness, the inner layer has a thickness, and a ratio of the thickness of the outer layer to the thickness of the inner layer is between about 1:1 to about 1:4.

13. A tampon comprising an insertion end; a withdrawal end; a withdrawal string extending from the withdrawal end; an absorbent structure and a multi-zoned foam cover substantially enclosing the absorbent structure, the cover comprising an outer zone having a first average pore size and capable of retaining fluids, and an inner zone having a second average pore size disposed between the outer zone and the absorbent structure; wherein the second average pore size is greater than the first average pore size; and wherein the inner zone creates a controlled interruption of fluid flow between the outer zone and the absorbent structure whereby the outer zone retains sufficient fluid to minimize vaginal wall drying prior to saturation of the absorbent structure.

* * * * *